United States Patent
Inoue et al.

(10) Patent No.: US 8,637,722 B2
(45) Date of Patent: Jan. 28, 2014

(54) ETHYLENE OLIGOMERIZATION CATALYST AND USE THEREOF

(75) Inventors: Koji Inoue, Ichihara (JP); Teruo Muraishi, Yokohama (JP); Phala Heng, Yokohama (JP)

(73) Assignee: Mitsui Chemicals, Inc., Tokyo (JP)

( * ) Notice: Subject to any disclaimer, the term of this patent is extended or adjusted under 35 U.S.C. 154(b) by 482 days.

(21) Appl. No.: 13/054,550

(22) PCT Filed: Jul. 22, 2009

(86) PCT No.: PCT/JP2009/063075
§ 371 (c)(1),
(2), (4) Date: Jan. 17, 2011

(87) PCT Pub. No.: WO2010/010879
PCT Pub. Date: Jan. 28, 2010

(65) Prior Publication Data
US 2011/0124938 A1 May 26, 2011

(30) Foreign Application Priority Data
Jul. 23, 2008 (JP) .................. 2008-189759

(51) Int. Cl.
*C07C 2/02* (2006.01)
*B01J 21/00* (2006.01)
*B01J 23/00* (2006.01)

(52) U.S. Cl.
USPC ........... 585/533; 502/259; 502/263; 502/335; 502/337; 502/439

(58) Field of Classification Search
USPC ........... 502/259, 263, 335, 337, 439; 585/533
See application file for complete search history.

(56) References Cited

U.S. PATENT DOCUMENTS

| | | | |
|---|---|---|---|
| 2,581,228 A * | 1/1952 | Bailey et al. | 502/259 |
| 2,904,608 A | 9/1959 | Holm et al. | |
| 2,921,971 A | 1/1960 | Holm et al. | |

(Continued)

FOREIGN PATENT DOCUMENTS

| | | |
|---|---|---|
| CN | 1141215 A | 1/1997 |
| CN | 101148391 A | 3/2008 |

(Continued)

OTHER PUBLICATIONS

J. Haveling, C. P. Nicolaides, M. S. Scurrell, Catalysts and conditions for the highly efficient, selective and stable heterogeneous oligomerization of ethylene, Elsevier, Applied Catalysis A, 1998 vol. 173, pp. 1-9.

(Continued)

*Primary Examiner* — Cam N. Nguyen
(74) *Attorney, Agent, or Firm* — Rankin, Hill & Clark LLP

(57) ABSTRACT

Ethylene is oligomerized with a catalyst in which nickel is supported on a support containing silica and alumina. The catalyst has little deterioration over long periods and affords oligomers with high productivity.

The ethylene oligomerization catalyst includes a support and a nickel compound supported on the support, the support including silica and alumina, and the amount of nickel supported is in the range of 0.0001 to 1 wt % based on the weight of the support, and the molar ratio of silica to alumina in the support ($SiO_2/Al_2O_3$) is in the range of 100 to 2000. In a process of the invention, ethylene is oligomerized with use of the catalyst.

10 Claims, 1 Drawing Sheet

(56) References Cited

U.S. PATENT DOCUMENTS

| | | | |
|---|---|---|---|
| 2,949,429 A | 8/1960 | Bailey et al. | |
| 3,045,054 A | 7/1962 | Holm et al. | |
| 3,216,952 A * | 11/1965 | Auguste et al. | 502/250 |
| 3,527,839 A | 9/1970 | Glockner et al. | |
| 4,293,725 A | 10/1981 | Beach et al. | |
| 4,538,012 A | 8/1985 | Miller | |
| 4,542,251 A | 9/1985 | Miller | |
| 4,575,575 A | 3/1986 | Drake et al. | |
| 4,740,645 A | 4/1988 | Garwood et al. | |
| 4,837,193 A * | 6/1989 | Akizuki et al. | 502/242 |
| 4,950,812 A * | 8/1990 | Jacobs et al. | 568/863 |
| 5,260,501 A | 11/1993 | Bhore et al. | |
| 5,607,890 A * | 3/1997 | Chen et al. | 502/202 |
| 5,723,713 A | 3/1998 | Maunders | |
| 5,883,036 A | 3/1999 | Fujie et al. | |
| 6,399,530 B1 * | 6/2002 | Chen et al. | 502/64 |
| 6,733,657 B2 * | 5/2004 | Benazzi et al. | 208/110 |
| 7,541,310 B2 * | 6/2009 | Espinoza et al. | 502/326 |
| 2007/0131586 A1 * | 6/2007 | Haan et al. | 208/110 |
| 2009/0018374 A1 * | 1/2009 | Bijlsma et al. | 568/959 |

FOREIGN PATENT DOCUMENTS

| | | |
|---|---|---|
| EP | 0133052 | 2/1985 |
| GB | 1117968 | 6/1968 |
| JP | 60-143830 | 7/1985 |
| JP | 2005-531658 | 10/2005 |
| JP | 2007-508935 | 4/2007 |
| WO | 93/06926 | 4/1993 |
| WO | 96/17811 | 6/1996 |

OTHER PUBLICATIONS

J. C. Mol, Industrial applications of olefin metathesis, Elsevier, Journal of Molecular Catalysis A: Chemical, 2004, vol. 213, pp. 39-45.

Catalysis and Zeolites, Fundamentals and Applications (edited by J. Weitkamp and L Puppe, Springer, 1999), pp. 127-155.

Chinese Office Action corresponding to CN application 200980128305.8 dated Sep. 5, 2012, eight pages.

C.P. Nicolaides et al., Nickel silica-alumina cataylsts for ethane oligomerization—control of the selectivity to 1-alkene products, Applied Catalysis A: General, May 30, 2003, vol. 245, No. 1, pp. 43-53.

M. Lallemand et al., Catalytic oligomerization of ethylene over Ni-containing dealuminated Y zeolites, Applied Catalysis A: General, Feb. 24, 2006, vol. 301, No. 2, pp. 196-201.

International Search Report Dated Oct. 27, 2009.

Extended European Search Report dated Dec. 15, 2011.

* cited by examiner

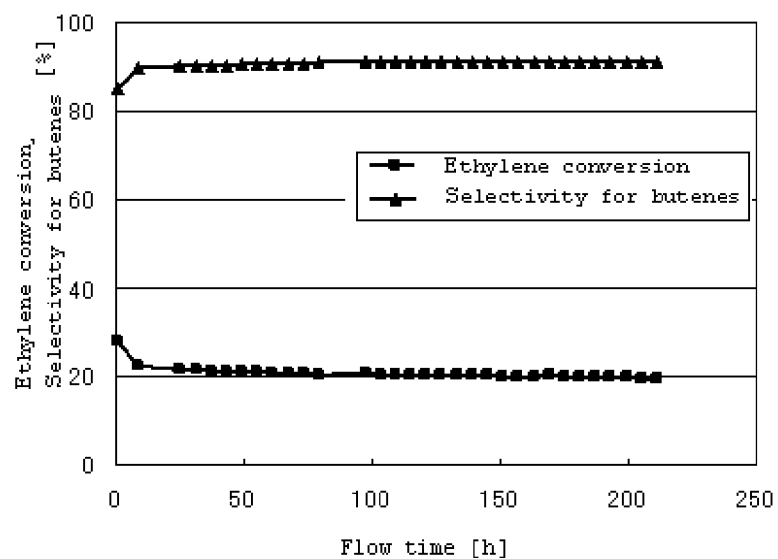

US 8,637,722 B2

ETHYLENE OLIGOMERIZATION CATALYST AND USE THEREOF

FIELD OF THE INVENTION

The present invention relates to ethylene oligomerization catalysts and uses thereof. In more detail, the invention relates to catalysts in which nickel is supported on a support including silica and alumina and the support has a large molar ratio of silica to alumina ($SiO_2/Al_2O_3$) and supports a very small amount of nickel, and which have ethylene oligomerization activity, in particular ethylene dimerization activity. The present invention also relates to ethylene oligomerization processes and olefin production processes using the catalysts.

BACKGROUND OF THE INVENTION

Liquid phase olefin oligomerization using catalysts consisting of a titanium or nickel complex and an alkylaluminum has been known. This oligomerization process, however, entails separating and recovering the catalysts and is thus complicated. Olefin oligomerization is also known to be performed by a liquid phase or gas phase process with use of catalysts in which nickel is supported on a support composed of silica, alumina, silica and alumina, or the like.

Patent Document 1 discloses catalysts wherein 0.1 to 5 wt % of nickel is supported on a support composed of silica and alumina (alumina content: 1 to 10 wt %). The silica/alumina molar ratio ($SiO_2/Al_2O_3$) is calculated to range from 15 to 168. It is described therein that the catalytic activity is not enhanced if the alumina content is less than 1 wt %, namely, if the silica/alumina molar ratio ($SiO_2/Al_2O_3$) exceeds 168.

Patent Documents 2 to 5 disclose catalysts obtained by coprecipitation of nickel, silica and alumina; catalysts obtained by supporting nickel on a silica/alumina support through impregnation cycles; and catalysts obtained by adding ammonium hydroxide to a nickel nitrate solution to obtain ammoniacal nickel and impregnating a silica/alumina support with the nickel. The nickel content in these catalysts is 2 wt % or more.

Patent Document 6 discloses catalysts wherein the nickel oxide/silica molar ratio is 0.001 or more and the silica/alumina molar ratio ($SiO_2/Al_2O_3$) ranges from 30 to 500. The nickel content is described to be 0.092 wt % or more. Preferred embodiments and working examples disclose 0.021 as a nickel oxide/silica molar ratio, and the nickel content is calculated therefrom to be 1.7 wt %.

Further, the catalysts of Patent Documents 2 to 6 have a problem of short life under high temperature reaction conditions. Furthermore, the catalysts of Patent Documents 1 to 6 easily decrease catalytic activity and induce isomerization to afford branched oligomers of low utility value.

Patent Document 7 discloses that a catalyst supporting nickel on a silica/alumina support is reacted with a sulfur-containing compound to afford a catalyst which supports nickel and sulfur on the support. However, the catalysts supporting nickel and sulfur show inferior activity to catalysts which support nickel alone.

Non-Patent Document 1 discloses catalysts wherein nickel is supported on a silica/alumina coprecipitated support by ion exchange. The catalysts are described to catalyze ethylene oligomerization under conditions such that the ethylene conversion is high at 90% or more. However, such high conversion conditions lead to an increased molecular weight of the oligomer due to successive reactions, and it is impossible to obtain low molecular oligomers such as dimers. Further, the catalysts permit long operation at a reaction temperature of 108° C., but a slight increase in reaction temperature to 127° C. causes irreversible deactivation.

Patent Document 1: U.S. Pat. No. 2,581,228
Patent Document 2: U.S. Pat. No. 2,921,971
Patent Document 3: U.S. Pat. No. 2,949,429
Patent Document 4: U.S. Pat. No. 3,045,054
Patent Document 5: U.S. Pat. No. 2,904,608
Patent Document 6: WO 93/06926
Patent Document 7: U.S. Pat. No. 3,527,839
Non-Patent Document 1: J. Haveling, C. P. Nicolaides, M. S. Scurrell, Catalysts and conditions for the highly efficient, selective and stable heterogeneous oligomerization of ethylene, ELSEVIER, Applied Catalysis A, 1998 Vol. 173, pp. 1-9

SUMMARY OF THE INVENTION

It is an object of the invention to provide catalysts in which a nickel compound is supported on a support containing silica and alumina, and which is capable of catalyzing oligomerization of ethylene to achieve high productivity for a long term with little catalyst deterioration.

The present inventors studied diligently to solve the problems in the art as described hereinabove. They have then found that catalysts have small deterioration and can afford oligomers with high productivity when a very small amount of nickel is supported on a silica/alumina support which has a very low alumina content, that is, has a large molar ratio of silica to alumina ($SiO_2/Al_2O_3$). The present invention has been completed based on the finding.

The present inventors worked hard in order to invent catalysts that show little deterioration over a long term and can produce oligomers with high productivity, and have found out a catalytic performance mechanism as follows.

Nickel works as a catalyst in the oligomerization of ethylene. However, when the nickel content is high as described in Patent Documents 2 to 6, nickel is aggregated and lowers activity and therefore a long catalyst life cannot be obtained. In particular, the nickel aggregation is facilitated under high temperature reaction conditions and is a critical factor that decreases the catalytic activity and life.

To enhance the catalytic activity and life, it is important to highly disperse nickel on a support as well as to stabilize nickel on the support. In the supports containing silica and alumina, alumina contributes to the stabilization of nickel. As long as the alumina content is small, the catalytic activity and catalyst life increase with increasing alumina content. When the alumina content is or is more than a certain level, however, the catalytic activity and life are lowered. In detail, a high alumina content corresponds to many acid sites on the catalyst surface. Cokes are accumulated at the acid sites on the catalyst surface, and the catalysts decrease catalytic activity and many acid sites induce isomerization to afford branched oligomers of low utility value.

The catalysts described in Patent Documents 1 to 6 have a small $SiO_2/Al_2O_3$ ratio, namely a high alumina content. Their acidic properties evoke undesired reactions such as coke generation and isomerization to afford branched oligomers, and cause lower catalytic activity and catalyst life.

It is therefore desired that the alumina content should be reduced to the minimum necessary. Meanwhile, alumina on the support stabilizes nickel, and therefore nickel stabilization is difficult when the molar number of nickel in the catalyst is in excess over that of alumina. It is thus preferred that the nickel/aluminum molar ratio (Ni/Al) in the catalyst is not far above 1. According to the invention, a very small amount of nickel is supported on a silica/alumina support which has a very low content of alumina, that is, has a large molar ratio of silica to alumina ($SiO_2/Al_2O_3$); whereby nickel is highly dispersed on the support stably and is less liable to aggregate. As a result, the catalysts according to the invention have little deterioration, high activity and long life.

The present invention is concerned with the following [1] to [10].

[1] An ethylene oligomerization catalyst comprising a support and a nickel compound supported on the support, the support containing silica and alumina, wherein:
the amount of nickel supported is in the range of 0.0001 to 1 wt % based on the weight of the support, and the molar ratio of silica to alumina in the support ($SiO_2/Al_2O_3$) is in the range of 100 to 2000.

[2] The ethylene oligomerization catalyst described in [1], wherein the molar ratio of nickel to aluminum in the catalyst (Ni/Al) is in the range of 0.00005 to 1.5.

[3] The ethylene oligomerization catalyst described in [1] or [2], wherein the amount of nickel supported is in the range of 0.0001 to 0.5 wt % based on the weight of the support, and the molar ratio of silica to alumina in the support ($SiO_2/Al_2O_3$) is in the range of 100 to 1000.

[4] The ethylene oligomerization catalyst described in any one of [1] to [3], wherein the molar ratio of silica to alumina in the support ($SiO_2/Al_2O_3$) is in the range of 150 to 1000.

[5] The ethylene oligomerization catalyst described in any one of [1] to [4], wherein the molar ratio of nickel to aluminum in the catalyst (Ni/Al) is in the range of 0.00005 to 1.2.

[6] The ethylene oligomerization catalyst described in any one of [1] to [5], wherein the amount of nickel supported is in the range of 0.0001 to less than 0.1 wt % based on the weight of the support.

[7] A process for producing ethylene oligomers, comprising oligomerizing ethylene in the presence of the oligomerization catalyst of any one of [1] to [6].

[8] A process for producing ethylene oligomers, comprising oligomerizing ethylene at a temperature of 100 to 400° C. and a pressure of 0.1 to 50 MPa with the oligomerization catalyst of any one of [1] to [6].

[9] The process described in [8], wherein the temperature is in the range of 150 to 350° C. and the pressure is in the range of 0.1 to 10 MPa.

[10] A process for producing olefins, comprising performing an oligomerization reaction by contacting ethylene with the oligomerization catalyst of any one of [1] to [6], and successively performing a disproportionation reaction by contacting the oligomers from the oligomerization reaction with ethylene in the presence of a disproportionation catalyst.

Advantageous Effects of the Invention

The catalysts of the invention are suited for ethylene oligomerization, are easily synthesized, and involve very small amounts of metals thereby providing economic advantages. The ethylene oligomerization processes with the catalysts of the invention can selectively synthesize, for example, 1-butene or 1-hexene from ethylene. 1-Butene and 1-hexene are useful comonomers for the production of polyethylenes, and butene is a useful material for the synthesis of propylene by disproportionation reaction with ethylene. The presence of isobutene with a branched structure is not preferable in the disproportionation reaction. The catalysts according to the invention permit selective synthesis of linear butenes.

The oligomerization processes with the catalysts of the invention enable long-term oligomer production with little catalyst deterioration and with high productivity.

The oligomerization catalysts according to the invention are resistant to deterioration over a long term even under high temperature reaction conditions. The olefin production processes of the invention involve a combination of the oligomerization catalyst with a disproportionation catalyst and thereby afford target olefins with high productivity. For example, ethylene is oligomerized into butene with the oligomerization catalyst, and the butene is reacted with unreacted ethylene in the presence of a disproportionation catalyst to afford propylene efficiently.

BRIEF DESCRIPTION OF THE DRAWING

FIG. 1 is a graph showing changes with time of ethylene conversion and selectivity for butenes in the reaction in Example 23.

PREFERRED EMBODIMENTS OF THE INVENTION

Ethylene Oligomerization Catalysts

Ethylene oligomerization catalysts according to the invention comprise a support containing silica and alumina, and a nickel compound supported on the support.

The amount of nickel supported is in the range of 0.0001 to 1 wt %, preferably 0.0001 to 0.5 wt %, more preferably 0.0001 to 0.13 wt %, and still more preferably 0.0001 to less than 0.1 wt %, based on the weight of the support. If the amount of nickel supported is below this range, oligomerization activity tends to be greatly lowered. If the nickel amount exceeds the above range, nickel is aggregated during the reaction and lowers oligomerization activity, and therefore the catalysts tend to fail ensure stable productivity over a long term.

The molar ratio of silica to alumina in the support ($SiO_2/Al_2O_3$) is in the range of 100 to 2000, preferably 100 to 1000, and more preferably 150 to 1000. If the silica/alumina molar ratio ($SiO_2/Al_2O_3$) is below this range, the catalysts have an increased number of acid sites and tend to afford a higher proportion of branched olefins, and cokes are accumulated on the catalyst surface to possibly lower the catalytic activity. If the silica/alumina molar ratio ($SiO_2/Al_2O_3$) exceeds the above range, a sufficient amount of alumina required to stabilize nickel cannot be ensured, and the catalysts tend to decrease oligomerization catalytic activity and catalyst life.

The molar ratio of nickel to aluminum in the catalyst (Ni/Al) is preferably in the range of 0.00005 to 1.5, more preferably 0.00005 to 1.2, and still more preferably 0.0005 to 1.0. If the nickel/aluminum molar ratio (Ni/Al) is below this range, the catalysts tend to fail to have sufficient catalytic activity. If the nickel/aluminum molar ratio (Ni/Al) exceeds the above range, a sufficient amount of alumina required to stabilize nickel cannot be ensured, and the catalytic activity and catalyst life tend to be lowered by nickel aggregation.

The supports in the invention are not limited as long as they contain silica and alumina and the silica/alumina molar ratio ($SiO_2/Al_2O_3$) is in the foregoing range.

The catalysts of the invention may be synthesized by various methods without limitation as long as the amount of nickel supported on the support is in the specified range. Preferably, the catalysts synthesized have a nickel/aluminum molar ratio (Ni/Al) in the above-described range.

Exemplary catalyst synthesizing processes include the following processes (i) to (vi):

Process (i) Coprecipitation from a solution containing a silica source compound, an alumina source compound and a nickel compound is carried out. The resultant precipitate is then filtered off, washed, dried and calcined.

Process (ii) Silica is impregnated with a solution of an alumina source compound and a nickel compound, and the solvent is distilled off. The residue is then dried and calcined.

Process (iii) A silica gel is mixed with a solution of an alumina source compound and a nickel compound, and the solvent is distilled off. The residue is then dried and calcined.

Process (iv) Silica is impregnated with a solution of an alumina source compound, and the solvent is distilled off. The residue is then dried and calcined. A nickel compound is supported on the calcined product by impregnation or ion exchange, followed by drying and calcination.

Process (v) A nickel compound is supported on a support containing silica and alumina by impregnation or ion exchange, followed by drying and calcination.

Process (vi) Nickel is supported on a support containing silica and alumina by CVD.

When the synthesis methods involve impregnation, the impregnation may be performed in one step or a plurality of steps.

The silica/alumina molar ratio ($SiO_2/Al_2O_3$) may be controlled to fall in the foregoing range by adjusting the amount of the alumina source compound relative to the mole number of silica calculated from the weight of the material silica in the above synthesis methods. Similarly, the nickel/aluminum molar ratio (Ni/Al) may be controlled to fall in the foregoing range by adjusting the amount of the nickel compound relative to the mole number of the alumina source compound.

The shapes of the catalysts in the invention are not particularly limited, and catalysts in various shapes may be used. The supports containing silica and alumina from the precipitation method are fine powders. A nickel compound may be supported on such powdery catalyst, or a nickel compound may be supported after the support containing silica and alumina is shaped.

Examples of the silica source compounds include silicates such as sodium silicate and alkoxysilanes, although not particularly limited thereto.

Examples of the alumina source compounds include aluminum nitrate and aluminum hydroxide, although not particularly limited thereto.

Examples of the nickel compounds include nickel acetate, nickel nitrate, nickel sulfate, nickel carbonate, nickel hydroxide, nickel halides, nickel acetylacetonate complexes and nickel phosphine complexes, although not particularly limited thereto. The nickel compounds may be used singly, or two or more kinds may be used in combination. Nickel nitrate and nickel sulfate are preferred. Specific examples of the nickel compounds include nickel nitrate hydrate and nickel sulfate hydrate.

The drying temperature in the synthesis methods is preferably in the range of 70 to 150° C., and more preferably 80 to 130° C. The drying time is preferably in the range of 0.1 to 50 hours, and more preferably 0.5 to 20 hours. The calcination temperature is preferably in the range of 200 to 800° C., and more preferably 200 to 700° C. The calcination time is preferably in the range of 0.1 to 300 hours, and more preferably 0.5 to 150 hours. This calcination time ensures that the catalyst life is increased while maintaining catalytic activity.

In the invention, silica supports having a high specific surface area and a high pore volume are preferably used. The specific surface area is preferably in the range of 200 to 1200 $m^2/g$, and the pore volume is preferably in the range of 0.4 to 2 cc/g. If these parameters are below these ranges, the obtainable catalysts tend to fail to show sufficient catalytic activity and catalyst life. If these parameters exceed the above ranges, the catalyst strength is insufficient and industrial use tends to be difficult. Silica supports having these properties may be conventional amorphous silicas, or may be mesoporous silicas such as MCM-41 and MCM-48 or zeolites with large pore diameters such as Y-zeolites, X-zeolites, mordenite, β-zeolites, L-zeolites and MFI.

Silicas may be commercially available or may be synthesized by carrying out precipitation from a solution containing a silica source, and filtering, drying and calcining the precipitate. When silicates such as sodium silicate are used, the precipitate may be washed with a solution containing an ammonium salt such as ammonium nitrate to substitute the sodium ions with ammonium ions and may be thereafter dried and calcined. The drying temperature is in the range of 70 to 150° C., and preferably 80 to 130° C. The calcination temperature is in the range of 200 to 800° C., and preferably 200 to 700° C.

Supports containing silica and alumina may also be synthesized by admixing a solution of an alumina source compound to a silica gel, distilling off the solvent, and drying and calcining the residue. Supports may be alternatively prepared by impregnating the silica obtained by the above-described method with a solution of an alumina source compound, then distilling off the solvent, and drying and calcining the residue. The drying temperature is in the range of 70 to 150° C., and preferably 80 to 130° C. The calcination temperature is in the range of 200 to 800° C., and preferably 200 to 700° C.

Still alternatively, supports may be prepared by coprecipitating silica and alumina from a mixture of a silica source compound and an alumina source compound, and filtering, drying and calcining the precipitate. The drying temperature is in the range of 70 to 150° C., and preferably 80 to 130° C. The calcination temperature is in the range of 200 to 800° C., and preferably 200 to 700° C.

Still alternatively, commercially available silica/alumina may be dealuminated into silica/alumina having a larger $SiO_2/Al_2O_3$ ratio. Exemplary dealumination methods include vapor treatment, silicon tetrachloride treatment and hexafluorosilicate treatment as described in Catalysis and Zeolites, Fundamentals and Applications (edited by J. Weitkamp and L. Puppe, Springer, 1999), pp. 127-155.

When the silica source compound contains an alumina source compound as an impurity, the silica source compound may be precipitated, filtered, dried and calcined; and the resulting compound may be used as a support containing silica and alumina, or alumina may be added thereto by the methods described hereinabove.

In a preferred embodiment in view of simple catalyst synthesis, commercially available silica may be impregnated with a solution of an alumina source compound, then the solvent may be distilled off and the residue may be dried and calcined, and thereafter nickel is supported on the calcined product by impregnating the calcined product with a nickel compound solution or by ion exchange.

<Processes for Producing Ethylene Oligomers>

In the processes for producing ethylene oligomers according to the present invention, ethylene is oligomerized with the oligomerization catalyst as described hereinabove.

In the ethylene oligomerization processes, raw material ethylene may contain paraffins, oxygen-containing compounds or water together. The raw material ethylene may be diluted with an inert gas such as helium, nitrogen or argon.

The oligomerization catalysts can efficiently catalyze the oligomerization reaction of ethylene into ethylene oligomers.

The ethylene oligomers produced by the processes of the invention include, for example, 1-butene, cis-2-butene, trans-2-butene, 3-methyl-1-pentene, 3-methyl-2-pentene, 4-methyl-1-pentene, 4-methyl-2-pentene, 1-hexene, 2-hexene, 3-hexene, 3,4-dimethyl-3-hexene, 3-methyl-3-heptene, 1-octene, 2-octene, 3-octene and 4-octene.

In the ethylene oligomerization processes, the ethylene oligomerization reaction may be performed with reactors of any types such as fixed bed reactors, fluidized bed reactors or moving bed reactors. Fixed bed reactors are preferable because of simple equipment. The oligomerization catalyst is packed in such reactors and ethylene is fed thereto and oligomerized.

The shapes of the oligomerization catalysts used in the ethylene oligomerization processes are not particularly limited, and catalysts in various shapes may be used. When the catalyst is fine powder, it may be packed in the fixed bed reactor directly or after physically mixed with a filler that is inert in the oligomerization reaction such as silica balls or alumina balls to avoid heavy pressure loss. Alternatively, fine powder of catalyst may be compacted, or may be shaped after kneaded with a sintering agent (a binder) that does not alter the catalytic performance.

Typical sintering agents are silica sintering agents, further alumina sintering agents, titania sintering agents, zirconia sintering agents or diatomaceous earth sintering agents may also be used. The sintering is preferably performed at temperatures of 500 to 800° C. Exemplary shapes include tablets, extrusions, pellets, spheres, microspheres, CDS extrusions, trilobes, quadlobes, rings, two-spoke rings, special spoke rings such as HGS, EW and LDP, rib rings and granules.

In the ethylene oligomerization processes, ethylene is oligomerized with the foregoing oligomerization catalyst generally at a temperature of 100 to 400° C. and a pressure of 0.1 to 50 MPa.

The oligomerization temperature is not particularly limited, but is generally in the range of 100 to 400° C., preferably 130 to 400° C., and more preferably 150 to 350° C. If the reaction temperature is below this range, by-products such as high-molecular oligomers will not smoothly diffuse away from the catalyst surface and the catalyst life tends to be reduced. If the reaction temperature exceeds the above range, nickel on the catalyst is aggregated and coke generation is accelerated, so that the lowering in catalytic activity tends to be accelerated.

In a preferred embodiment, the catalyst is activated prior to the reaction by supplying an inert gas such as helium, nitrogen or argon into the heated reactor. The heating temperature is in the range of 100 to 600° C., and preferably 200 to 500° C. The heating time ranges from 0.1 to 10 hours, and preferably 1 to 5 hours.

After the catalyst is activated with an inert gas, it may be further treated with raw material ethylene or a reducing gas such as hydrogen. The treatment temperature is in the range of 200 to 600° C., and preferably 300 to 600° C. The treatment time ranges from 0.1 to 20 hours, and preferably 0.1 to 10 hours. This treatment increases the catalyst life without deteriorating the catalytic activity.

The pressure in the oligomerization reaction is not particularly limited, but is generally in the range of 0.1 to 50 MPa, preferably 0.1 to 10 MPa, and more preferably 0.1 to 5 MPa. If the pressure is below this range, establishing a highly efficient process tends to be difficult. A pressure exceeding the above range tends to cause an increased amount of by-products.

The weight hourly space velocity (WHSV) of ethylene per unit catalyst weight is preferably in the range of 0.1 to 50 $h^{-1}$, more preferably 0.5 to 40 $h^{-1}$, and still more preferably 0.5 to 30 $h^{-1}$. If the WHSV is below this range, the productivity tends to be lowered and successive oligomerization reactions take place progressively possibly to lower the selectivity for dimers or trimers. If the WHSV exceeds the above range, the ethylene conversion tends to be lowered.

A single reactor or a plurality of reactors may be used. In the case of plural reactors, a parallel arrangement of the reactors allows for constant production by switching oligomerization reaction in one reactor and catalyst regeneration in other reactor.

The reaction product may be separated and purified from unreacted ethylene or high-boiling oligomers by known methods such as distillation, extraction and adsorption. The unreacted ethylene may be recycled to the reactor.

To regenerate the catalyst, for example, the supply of ethylene is suspended, the reactor is purged with an inert gas such as helium, nitrogen or argon, and an inert gas such as helium, nitrogen or argon that contains 0.1 to 20% by volume of oxygen is passed through the reactor at 300 to 700° C., preferably 400 to 600° C. for 0.1 to 100 hours, preferably 0.5 to 50 hours. The gas flow rate may be in the range of 1 to 100 ml/min, and preferably 10 to 80 ml/min.

The ethylene oligomerization catalysts of the invention may be effectively used also for the dimerization of ethylene. The ethylene dimerization may be carried out under the conditions as described hereinabove, but dimers may be produced with high selectivity when the reaction is performed under conditions such that the ethylene conversion will be lower than in usual oligomerization reactions. For example, such lower ethylene conversion may be achieved by controlling the amount of nickel supported on the oligomerization catalyst.

<Olefin Production Processes>

In the processes for producing olefins according to the invention, an oligomerization reaction is carried out by contacting ethylene with the oligomerization catalyst as described above, and successively a disproportionation reaction is conducted by contacting the oligomer from the oligomerization reaction with ethylene in the presence of a disproportionation catalyst.

According to the olefin production processes of the invention, ethylene as a raw material may be converted efficiently and economically into an olefin having a different number of carbon atoms from the raw material ethylene (hereinafter, resultant olefin).

The resultant olefins produced by the processes of the invention include, for example, propylene, 1-butene, cis-2-butene, trans-2-butene, 1-pentene, 2-pentene, 3-methyl-1-butene, 2-methyl-1-butene and 2-methyl-2-butene.

The olefin production processes use the foregoing oligomerization catalysts that have little deterioration over long periods even under high temperature oligomerization conditions. Hence, the oligomerization reaction in the olefin production processes may be generally carried out at 100 to 400° C., and are preferably performed under high temperature conditions such as 130 to 400° C., and more preferably 150 to 350° C.

The disproportionation catalysts used in the olefin production processes are not particularly limited, and known such catalysts may be used with examples including catalysts disclosed in U.S. Pat. No. 4,575,575. Cocatalysts may be used in combination with the disproportionation catalysts. The cocatalysts are not particularly limited, and cocatalysts disclosed in U.S. Pat. No. 4,575,575 may be used.

The disproportionation temperature may be for example as described in U.S. Pat. No. 4,575,575. Industrial disproportionation reactions are generally carried out under high temperature conditions such as 260° C. or above (e.g., J. C. Mol, Industrial applications of olefin metathesis, ELSEVIER, Journal of Molecular Catalysis A: Chemical, 2004, Vol. 213, pp. 39-45).

In the olefin production processes, the oligomerization catalysts permit the oligomerization reaction to be performed at high temperatures. The resultant oligomer at a high temperature is successively brought into contact with the unreacted raw material ethylene in the presence of the disproportionation catalyst, whereby the heating energy required for the disproportionation reaction can be reduced to the minimum necessary. Therefore, the olefin production processes of the invention efficiently and economically provide target resultant olefins from ethylene as raw material.

In the disproportionation of the olefin from the processes for producing ethylene oligomers of the invention and unreacted ethylene, the ethylene oligomerization and the subsequent disproportionation reaction may be carried out in the same or differing reactors. When they are conducted in the same reactor, the oligomerization catalyst and the disproportionation catalyst may be continually packed in the reactor or may have a filler therebetween that is inert in the oligomerization and disproportionation reactions such as quartz sand. The reaction temperature is generally in the range of 100 to 400° C., preferably 130 to 400° C., and more preferably 150 to 350° C. The reaction pressure is preferably in the range of 0.1 to 50 MPa, and more preferably 0.1 to 10 MPa.

When the ethylene oligomerization reaction and the disproportionation reaction are carried out in respective reactors, the oligomerization catalyst is packed in an oligomerization reactor and ethylene is oligomerized therein, and the resultant oligomer and unreacted ethylene are fed to a disproportionation reactor containing the disproportionation catalyst, thereby producing resultant olefin. Where necessary, a step for removing by-products other than the oligomer and unreacted ethylene may be performed between the ethylene oligomerization reaction and the disproportionation reaction. In performing the disproportionation reaction, raw material ethylene may be added to the unreacted ethylene. The oligomer from the oligomerization reaction may be purified by known methods such as distillation, extraction and adsorption and may be supplied to the disproportionation reactor together with raw material ethylene.

The ethylene oligomerization temperature is generally in the range of 100 to 400° C., preferably 130 to 400° C., and more preferably 150 to 350° C.; and the reaction pressure is preferably in the range of 0.1 to 50 MPa, and more preferably 0.1 to 10 MPa. The disproportionation temperature and pressure are not particularly limited, and may be as described in U.S. Pat. No. 4,575,575.

The ethylene oligomerization reaction and the disproportionation reaction in respective reactors may be each carried out under optimum conditions.

The product from the disproportionation reaction may be separated and purified from unreacted ethylene and oligomers from the oligomerization by known methods such as distillation, extraction and adsorption. The unreacted ethylene may be recycled to the oligomerization reaction or the disproportionation reaction. The oligomers from the oligomerization reaction may be recycled to the disproportionation reaction.

In the oligomerization and disproportionation reactions, the raw material ethylene may contain hydrogen gas as described in British Patent No. 1117968.

EXAMPLES

The present invention will be described in greater detail hereinbelow without limiting the scope of the invention.

The amount of nickel supported and the silica/alumina molar ratio ($SiO_2/Al_2O_3$) were determined quantitatively with an ICP emission spectrometer (VISTA-PRO manufactured by Seiko Instruments Inc.), an ICP mass spectrometer (Agilent 7500s manufactured by Agilent Technologies Inc.) or an atomic absorption photometer (Z-5000 manufactured by Hitachi, Ltd.). Unreacted raw materials and reaction products were quantified by gas chromatography.

The catalyst life was defined as the time until the initial ethylene conversion lowered 10%.

Example 1

(1) Preparation of Support 0.0525 g of aluminum hydroxide and 1.0 g of sodium hydroxide were added to 1.5 ml of distilled water and were heated under reflux to give a transparent aqueous solution. Additional 50 ml of distilled water was added, and the mixture was heated with stirring to form a homogeneous aqueous solution. To the aqueous solution, there were added an aqueous solution of 55.7 g of water glass (No. 3) in 217 ml of distilled water, and 110 ml of 1.4 M nitric acid. The mixture was vigorously stirred at room temperature and was aged for 3 days. Thereafter, the solid was filtered and was washed with water.

The solid was added to 300 ml of a 1 M aqueous ammonium nitrate solution. The mixture was stirred at 50° C. for 1 hour and was aged at room temperature overnight. The solid formed was filtered, washed with water, dried at 80° C. in air for 18 hours, and calcined at 500° C. for 3 hours to afford 13.26 g of a support containing silica and alumina.

(2) Preparation of Catalyst 2.0 g of the support obtained in (1) above was suspended in 20 ml of distilled water. Subsequently, 20 ml of an aqueous solution containing 0.044 g of nickel nitrate hexahydrate was added to the suspension, followed by stirring at room temperature for 1 hour and heating at 80° C. for 20 hours. The temperature was lowered to room temperature, and the solid formed was filtered, washed with water, dried at 80° C. in air for 3 hours, and calcined at 500° C. for 6 hours to afford a catalyst.

The catalyst was found to contain 0.13 wt % of nickel relative to the support weight and have a silica/alumina molar ratio (hereinafter, also $SiO_2/Al_2O_3$) of 640 and a nickel/aluminum molar ratio (hereinafter, also Ni/Al) of 0.50. Properties of the catalyst obtained are set forth in Table 1.

(3) Oligomerization Reaction

A fixed bed flow reactor (stainless steel, inner diameter: 9.5 mm, length: 250 mm) was used. The fixed bed flow reactor was packed with 0.300 g of the catalyst obtained in (2) above, together with quartz wool and quartz sand as holding materials, so that the total length of the packings became 250 mm. Nitrogen was passed through the reactor at a rate of 50 ml/min at atmospheric pressure, and the catalyst layer was held at 300° C. for 2 hours. The gas flow was changed from nitrogen to ethylene, which was fed at 300° C., 0.1 MPa and WHSV of 6.13 $h^{-1}$, and thereby ethylene was oligomerized. After the reaction for 24 hours, the ethylene conversion was 19.8%, the selectivity for butenes was 84.6%, and the selectivity for hexenes was 9.2%. The catalyst life was 24 hours. The results are set forth in Table 2.

Example 2

A catalyst was prepared in the same manner as in Example 1, except that the amount of the support obtained in Example 1 (1) was changed from 2.0 g to 1.0 g, and that 0.044 g of nickel nitrate hexahydrate was replaced by 0.020 g of nickel sulfate hexahydrate. Properties of the catalyst are set forth in Table 1. Reaction was performed as described in Example 1 (3), except that the above catalyst was used. After the reaction for 24 hours, the ethylene conversion was 20.0%, the selectivity for butenes was 84.0%, and the selectivity for hexenes was 9.6%. The catalyst life was 53 hours. The results are set forth in Table 2.

Example 3

A catalyst was prepared in the same manner as in Example 2, except that 0.020 g of nickel sulfate hexahydrate was replaced by 0.018 g of nickel chloride hexahydrate. Properties of the catalyst are set forth in Table 1. Reaction was performed as described in Example 1 (3), except that the above catalyst was used. After the reaction for 24 hours, the ethylene conversion was 19.1%, the selectivity for butenes was 84.3%, and the selectivity for hexenes was 9.4%. The catalyst life was 30 hours. The results are set forth in Table 2.

Example 4

A catalyst was prepared in the same manner as in Example 1, except that 0.044 g of nickel nitrate hexahydrate was replaced by 0.038 g of nickel acetate tetrahydrate. Properties of the catalyst are set forth in Table 1. Reaction was performed as described in Example 1 (3), except that the above catalyst was used. After the reaction for 24 hours, the ethylene conversion was 18.0%, the selectivity for butenes was 84.5%, and the selectivity for hexenes was 9.3%. The catalyst life was 20 hours. The results are set forth in Table 2.

Example 5

(1) Preparation of Support 2.8 g of CARIACT G130 pellets (manufactured by FUJI SILYSIA CHEMICAL LTD.) were suspended in 11 ml of distilled water, and 2.8 ml of an aqueous solution containing 0.07 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 20 ml of an aqueous solution containing 0.0044 g of nickel nitrate hexahydrate was added to the suspension, followed by stirring at room temperature for 10 minutes and heating at 80° C. for 20 hours. The temperature was lowered to room temperature, and the solid formed was filtered, washed with water, dried at 80° C. for 3 hours, and calcined at 300° C. for 6 hours to afford a catalyst.

The catalyst was found to contain 0.038 wt % of nickel relative to the support weight and have $SiO_2/Al_2O_3$ of 621 and Ni/Al of 0.13. Properties of the catalyst obtained are set forth in Table 1.

(3) Oligomerization Reaction

Reaction was performed as described in Example 1 (3), except that the catalyst obtained in (2) above was used. After the reaction for 28 hours, the ethylene conversion was 29.2%, the selectivity for butenes was 86.4%, and the selectivity for hexenes was 8.9%. The catalyst life was 70 hours. The results are set forth in Table 2.

Example 6

(1) Preparation of Support 3.0 g of CARIACT Q-6 (manufactured by FUJI SILYSIA CHEMICAL LTD.) was suspended in 12 ml of distilled water, and 3 ml of an aqueous solution containing 0.075 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 20 ml of an aqueous solution containing 0.0044 g of nickel nitrate hexahydrate was added to the suspension, followed by stirring at room temperature for 10 minutes and heating at 80° C. for 20 hours. The temperature was lowered to room temperature, and the solid formed was filtered, washed with water, dried at 80° C. in air for 3 hours, and calcined at 300° C. for 6 hours to afford a catalyst.

Properties of the catalyst obtained are set forth in Table 1.

(3) Oligomerization Reaction

Reaction was performed as described in Example 1 (3), except that the catalyst obtained in (2) above was used. The results after the reaction for 24 hours are set forth in Table 2.

Example 7

(1) Preparation of Support 5.0 g of Sylosphere 1504 (manufactured by FUJI SILYSIA CHEMICAL LTD.) was suspended in 20 ml of distilled water, and 5 ml of an aqueous solution containing 0.125 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 20 ml of an aqueous solution containing 0.0022 g of nickel nitrate hexahydrate was added to the suspension, followed by stirring at room temperature for 10 minutes and heating at 80° C. for 20 hours. The temperature was lowered to room temperature, and the solid formed was filtered, washed with water, dried at 80° C. in air for 3 hours, and calcined at 300° C. for 6 hours to afford a catalyst.

The catalyst was found to contain 0.02 wt % of nickel relative to the support weight and have $SiO_2/Al_2O_3$ of 532 and Ni/Al of 0.07. Properties of the catalyst obtained are set forth in Table 1.

(3) Oligomerization Reaction

A fixed bed flow reactor (stainless steel, inner diameter: 9.5 mm, length: 250 mm) was used. The fixed bed flow reactor was packed with 0.275 g of the catalyst obtained in (2) above, together with quartz wool and quartz sand as holding materials, so that the total length of the packings became 250 mm. Nitrogen was passed through the reactor at a rate of 50 ml/min at atmospheric pressure, and the catalyst layer was held at 300° C. for 2 hours. The temperature of the catalyst layer was lowered to 250° C., and the gas flow was changed from nitrogen to ethylene, which was fed at 250° C., 0.35 MPa and WHSV of 6.67 $h^{-1}$, and thereby ethylene was oligomerized. After the reaction for 24 hours, the ethylene conversion was 21.8%, the selectivity for butenes was 89.9%, and the selectivity for hexenes was 8.0%. The catalyst life was 310 hours. The results are set forth in Table 2.

Comparative Example 1

A catalyst was prepared in the same manner as in Example 1, except that aluminum hydroxide was not used. Properties of the catalyst are set forth in Table 1. Reaction was performed as described in Example 1 (3), except that the above catalyst was used. The results after the reaction for 24 hours are set forth in Table 2. Ethylene did not undergo the reaction. This result was probably due to a high Ni/Al ratio of 6.13.

Comparative Example 2

1.0 g of γ-alumina (manufactured by Sumitomo Chemical Co., Ltd.) was suspended in 10 ml of distilled water, and 2.5 ml of an aqueous solution containing 0.055 g of nickel sulfate hexahydrate was added to the suspension. The mixture was stirred at room temperature for 10 minutes, and water was distilled away. The solid thus formed was dried at 110° C. in air for 3 hours and was continuously dried at the temperature for 1 hour in an atmosphere purged with nitrogen. Thereafter, the solid was calcined at 510° C. for 16 hours in the nitrogen atmosphere to afford a catalyst. Properties of the catalyst obtained are set forth in Table 1. Reaction was performed as described in Example 1 (3), except that the above catalyst was used. The results after the reaction for 18 hours are set forth in Table 2. Ethylene did not undergo the reaction. This result was probably due to an extremely low Ni/Al ratio.

Comparative Example 3

97 ml of an aqueous solution containing 2.80 g of nickel nitrate hexahydrate was added to 10 g of ZSM-5 ($NH_4$ type, manufactured by ZEOLYST, $SiO_2/Al_2O_3$=50), followed by stirring at room temperature for 5 minutes and heating at 80° C. for 5 hours. The temperature was lowered to room temperature, and the solid formed was filtered, washed with water, dried at 120° C. in air for 4 hours, and calcined at 500° C. for 6 hours to afford a catalyst. Properties of the catalyst obtained are set forth in Table 1. Reaction was performed as described in Example 1 (3), except that the above catalyst was used. After the reaction for 27 hours, the ethylene conversion was 11.5%, the selectivity for butenes was 31.3%, and the selectivity for hexenes was 14.9%. The catalyst life was 3 hours. The results are set forth in Table 2. The low catalytic activity in Comparative Example 3 was probably due to a low $SiO_2/Al_2O_3$ ratio.

Comparative Example 4

(1) Preparation of Support 0.9 g of aluminum hydroxide and 1.0 g of sodium hydroxide were added to 1.5 ml of distilled water and were heated under reflux to give a transparent aqueous solution. Additional 50 ml of distilled water was added, and the mixture was heated with stirring to form a homogeneous aqueous solution. To the aqueous solution, there were added an aqueous solution of 55.7 g of water glass (No. 3) in 217 ml of distilled water, and 110 ml of 1.4 M nitric acid. The mixture was vigorously stirred at room temperature and was aged for 3 days. Thereafter, the solid was filtered and was washed with water.

The solid was added to 500 ml of a 1 M aqueous ammonium nitrate solution. The mixture was stirred at 50° C. for 1 hour and was aged at room temperature overnight. The solid formed was filtered, washed with water, dried at 80° C. in air for 18 hours, and calcined at 550° C. for 3 hours to afford 16.8 g of a support containing silica and alumina.

(2) Preparation of Catalyst 2.0 g of the support obtained in (1) above was suspended in 20 ml of distilled water. Subsequently, 20 ml of an aqueous solution containing 0.044 g of nickel nitrate hexahydrate was added to the suspension, followed by stirring at room temperature for 10 minutes. Water was distilled away at 70° C. under reduced pressure. The solid formed was dried at 80° C. for 18 hours and was calcined at 500° C. for 6 hours to afford a catalyst. Properties of the catalyst obtained are set forth in Table 1.

(3) Oligomerization Reaction

Reaction was performed as described in Example 1 (3), except that the catalyst obtained in (2) above was used. After the reaction for 27 hours, the ethylene conversion was 23.2%, the selectivity for butenes was 83.3%, and the selectivity for hexenes was 10.0%. The catalyst life was 6 hours. The results are set forth in Table 2. The low catalytic activity in Comparative Example 4 was probably due to a low $SiO_2/Al_2O_3$ ratio.

TABLE 1

|  | Amount of nickel supported (wt %) | $SiO_2/Al_2O_3$ (mol/mol) | Ni/Al (mol/mol) |
|---|---|---|---|
| Ex. 1 | 0.13 | 640 | 0.50 |
| Ex. 2 | 0.11 | 650 | 0.39 |
| Ex. 3 | 0.11 | 590 | 0.36 |
| Ex. 4 | 0.16 | 547 | 0.57 |
| Ex. 5 | 0.038 | 621 | 0.13 |
| Ex. 6 | 0.042 | 487 | 0.13 |
| Ex. 7 | 0.02 | 532 | 0.07 |
| Comp. Ex. 1 | 0.40 | 2177 | 6.13 |
| Comp. Ex. 2 | 0.18 | 0 | <0.0005 |
| Comp. Ex. 3 | 0.17 | 50 | 0.05 |
| Comp. Ex. 4 | 0.44 | 37 | 0.11 |

TABLE 2

| | Reaction temperature (°C.) | Reaction pressure (MPa) | WHSV (h$^{-1}$) | Ethylene conversion (%) | Selectivity for butenes (%) | Selectivity for hexenes (%) | Life (h) |
|---|---|---|---|---|---|---|---|
| Ex. 1 | 300 | 0.1 | 6.13 | 19.8 | 84.6 | 9.2 | 24 |
| Ex. 2 | 300 | 0.1 | 6.13 | 20.0 | 84.0 | 9.6 | 53 |
| Ex. 3 | 300 | 0.1 | 6.13 | 19.1 | 84.3 | 9.4 | 30 |
| Ex. 4 | 300 | 0.1 | 6.13 | 18.0 | 84.5 | 9.3 | 20 |
| Ex. 5 | 300 | 0.1 | 6.13 | 29.2[1] | 86.4[1] | 8.9[1] | 70 |
| Ex. 6 | 300 | 0.1 | 6.13 | 28.5 | 86.4 | 9.0 | 70 |
| Ex. 7 | 250 | 0.35 | 6.67 | 21.8 | 89.9 | 8.0 | 310 |
| Comp. Ex. 1 | 300 | 0.1 | 6.13 | 0 | — | — | — |
| Comp. Ex. 2 | 300 | 0.1 | 6.13 | 0[2] | — | — | — |
| Comp. Ex. 3 | 300 | 0.1 | 6.13 | 11.5[3] | 31.3[3] | 14.9[3] | 3 |
| Comp. Ex. 4 | 300 | 0.1 | 6.13 | 23.2 | 83.3 | 10.0 | 6 |

[1] Date after the reaction for 28 hours
[2] Data after the reaction for 18 hours
[3] Data after the reaction for 27 hours Example 8

(1) Preparation of Support 5.0 g of CARIACT Q-6 (manufactured by FUJI SILYSIA CHEMICAL LTD.) was suspended in 20 ml of distilled water, and 5 ml of an aqueous solution containing 0.125 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 20 ml of an aqueous solution containing 0.0044 g of nickel nitrate hexahydrate was added to the suspension, followed by stirring at room temperature for 1 hour and heating at 80° C. for 20 hours. The temperature was lowered to room temperature, and the solid formed was filtered, washed with water, dried at 80° C. in air for 3 hours, and calcined at 300° C. for 6 hours to afford a catalyst.

The catalyst was found to contain 0.038 wt % of nickel relative to the support weight and have $SiO_2/Al_2O_3$ of 521 and Ni/Al of 0.12. Properties of the catalyst obtained are set forth in Table 3.

(3) Oligomerization Reaction

Reaction was performed as described in Example 1 (3), except that the catalyst obtained in (2) above was used. After the reaction for 24 hours, the ethylene conversion was 21.7%, the selectivity for butenes was 86.9%, and the selectivity for hexenes was 8.4%. The catalyst life was 264 hours. The results are set forth in Table 4.

Example 9

A fixed bed flow reactor (stainless steel, inner diameter: 9.5 mm, length: 250 mm) was used. The fixed bed flow reactor was packed with 0.275 g of the catalyst obtained in Example 8 (2), together with quartz wool and quartz sand as holding materials, so that the total length of the packings became 250 mm. Nitrogen was passed through the reactor at a rate of 50 ml/min at atmospheric pressure, and the catalyst layer was held at 300° C. for 2 hours. The gas flow was changed from nitrogen to ethylene, which was fed at 300° C., 0.35 MPa and WHSV of 6.67 h$^{-1}$, and thereby ethylene was oligomerized. After the reaction for 27.5 hours, the ethylene conversion was 37.7%, the selectivity for butenes was 82.7%, and the selectivity for hexenes was 11.7%. The catalyst life was 18 hours. The results are set forth in Table 4.

Example 10

(1) Preparation of Support 3.0 g of Silica SS 62138 (manufactured by Saint-Gobain K.K.) was suspended in 12 ml of distilled water, and 3 ml of an aqueous solution containing 0.075 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 20 ml of an aqueous solution containing 0.0044 g of nickel nitrate hexahydrate was added to the suspension, followed by stirring at room temperature for 10 minutes and heating at 80° C. for 20 hours. The temperature was lowered to room temperature, and the solid formed was filtered, washed with water, dried at 80° C. in air for 3 hours, and calcined at 300° C. for 6 hours to afford a catalyst.

The catalyst was found to contain 0.035 wt % of nickel relative to the support weight and have $SiO_2/Al_2O_3$ of 470 and Ni/Al of 0.09. Properties of the catalyst obtained are set forth in Table 3.

(3) Oligomerization Reaction

Reaction was performed as described in Example 1 (3), except that the catalyst obtained in (2) above was used. After the reaction for 24 hours, the ethylene conversion was 29.4%, the selectivity for butenes was 86.7%, and the selectivity for hexenes was 9.0%. The catalyst life was 72 hours. The results are set forth in Table 4.

Example 11

(1) Preparation of Support 5.0 g of Silica SS 62138 (manufactured by Saint-Gobain K.K.) was suspended in 20 ml of distilled water, and 10 ml of an aqueous solution containing 0.250 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 20 ml of an aqueous solution containing 0.0044 g of nickel nitrate hexahydrate was added to the suspension, followed by stirring at room temperature for 10 minutes and heating at 80° C. for 20 hours. The temperature was lowered to room temperature, and the solid formed was filtered, washed with water, dried at 80° C. in air for 3 hours, and calcined at 500° C. for 6 hours to afford a catalyst.

The catalyst was found to contain 0.043 wt % of nickel relative to the support weight and have $SiO_2/Al_2O_3$ of 275 and Ni/Al of 0.07. Properties of the catalyst obtained are set forth in Table 3.

(3) Oligomerization Reaction

Reaction was performed as described in Example 9, except that the catalyst obtained in (2) above was used. After the reaction for 24 hours, the ethylene conversion was 45.2%, the selectivity for butenes was 80.9%, and the selectivity for hexenes was 13.1%. The catalyst life was 21 hours. The results are set forth in Table 4.

Example 12

(1) Preparation of Support 10.0 g of Silica SS 62138 (manufactured by Saint-Gobain K.K.) was suspended in 40 ml of distilled water, and 10 ml of an aqueous solution containing 0.50 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 8.8 g of the support obtained in (1) above was suspended in 88 ml of distilled water. Subsequently, 44 ml of an aqueous solution containing 0.020 g of nickel nitrate hexahydrate was added to the suspension, followed by stirring at room temperature for 10 minutes and heating at 80° C. for 20 hours. The temperature was lowered to room temperature, and the solid formed was filtered, washed with water, dried at 80° C. in air for 3 hours, and calcined at 500° C. for 6 hours to afford a catalyst.

The catalyst was found to contain 0.04 wt % of nickel relative to the support weight and have $SiO_2/Al_2O_3$ of 243 and Ni/Al of 0.06. Properties of the catalyst obtained are set forth in Table 3.

(3) Oligomerization Reaction

A fixed bed flow reactor (stainless steel, inner diameter: 9.5 mm, length: 250 mm) was used. The fixed bed flow reactor was packed with 0.275 g of the catalyst obtained in (2) above, together with quartz wool and quartz sand as holding materials, so that the total length of the packings became 250 mm. In this example, nitrogen and hydrogen were used together for the pretreatment before the reaction. In detail, nitrogen was passed through the reactor at a rate of 50 ml/min at atmospheric pressure, and the catalyst layer was held at 550° C. for 1 hour. Subsequently, a gas mixture containing 50% nitrogen and 50% hydrogen was passed through the reactor at a rate of 100 ml/min at atmospheric pressure, and the catalyst layer was held at 550° C. for 0.5 hour. While the temperature of the catalyst layer was lowered, nitrogen alone was passed at a rate of 50 ml/min at atmospheric pressure. When the temperature of the catalyst layer became 300° C., the gas flow was changed from nitrogen to ethylene, which was fed at 300° C., 0.35 MPa and WHSV of 6.67 $h^{-1}$, and thereby ethylene was oligomerized. After the reaction for 24 hours, the ethylene conversion was 44.1%, the selectivity for butenes was 81.8%, and the selectivity for hexenes was 11.1%. The catalyst life was 30 hours. The results are set forth in Table 4.

It was demonstrated that the pretreatment with hydrogen increased the catalyst life while the activity was maintained.

TABLE 3

|  | Amount of nickel supported (wt %) | $SiO_2/Al_2O_3$ (mol/mol) | Ni/Al (mol/mol) |
|---|---|---|---|
| Ex. 8 | 0.038 | 521 | 0.12 |
| Ex. 9 | 0.038 | 521 | 0.12 |
| Ex. 10 | 0.035 | 470 | 0.09 |
| Ex. 11 | 0.043 | 275 | 0.07 |
| Ex. 12 | 0.04 | 243 | 0.06 |

TABLE 4

|  | Reaction temperature (° C.) | Reaction pressure (MPa) | WHSV ($h^{-1}$) | Ethylene conversion (%) | Selectivity for butenes (%) | Selectivity for hexenes (%) | Life (h) |
|---|---|---|---|---|---|---|---|
| Ex. 8 | 300 | 0.1 | 6.13 | 21.7 | 86.9 | 8.4 | 264 |
| Ex. 9 | 300 | 0.35 | 6.67 | 37.7[1)] | 82.7[1)] | 11.7[1)] | 18 |
| Ex. 10 | 300 | 0.1 | 6.13 | 29.4 | 86.7 | 9.0 | 72 |
| Ex. 11 | 300 | 0.35 | 6.67 | 45.2 | 80.9 | 13.1 | 21 |
| Ex. 12 | 300 | 0.35 | 6.67 | 44.1 | 81.8 | 11.1 | 30 |

[1)]Date after the reaction for 27.5 hours

Example 13

A catalyst was prepared in the same manner as in Example 10, except that the catalyst calcination time after the addition of nickel nitrate hexahydrate was changed from 6 hours to 24 hours. The catalyst was found to contain 0.035 wt % of nickel relative to the support weight and have $SiO_2/Al_2O_3$ of 470 and Ni/Al of 0.09.

Reaction was performed as described in Example 11, except that the above catalyst was used. After the reaction for 24 hours, the ethylene conversion was 38.7%, the selectivity for butenes was 82.0%, and the selectivity for hexenes was 12.2%. The catalyst life was 50 hours. The results are set forth in Table 6.

Example 14

A catalyst was prepared in the same manner as in Example 13, except that the catalyst calcination time was changed from 24 hours to 60 hours. The catalyst was found to contain 0.035 wt % of nickel relative to the support weight and have $SiO_2/Al_2O_3$ of 470 and Ni/Al of 0.09.

Reaction was performed as described in Example 11, except that the above catalyst was used. After the reaction for 24 hours, the ethylene conversion was 35.6%, the selectivity for butenes was 83.2%, and the selectivity for hexenes was 11.2%. The catalyst life was 50 hours. The results are set forth in Table 6.

The results of Examples 13 and 14 showed that the catalysts achieved an increased catalyst life when calcined for 24 hours or more while the catalytic activity was maintained.

TABLE 5

| | Reaction temperature (° C.) | Reaction pressure (MPa) | WHSV (h$^{-1}$) | Ethylene conversion (%) | Selectivity for butenes (%) | Selectivity for hexenes (%) | Life (h) |
|---|---|---|---|---|---|---|---|
| Ex. 11 | 300 | 0.35 | 6.67 | 45.2 | 80.9 | 13.1 | 21 |
| Ex. 13 | 300 | 0.35 | 6.67 | 38.7 | 82.0 | 12.2 | 50 |
| Ex. 14 | 300 | 0.35 | 6.67 | 35.6 | 83.2 | 11.2 | 50 |

Example 15

The catalyst used in Example 14 was regenerated by passing a gas mixture containing 96% nitrogen and 4% oxygen at a rate of 45 ml/min under atmospheric pressure at 500° C. for 2 hours. The regenerated catalyst was used to catalyze a reaction similarly to Example 14. The regenerated catalyst maintained a performance equivalent to that before the regeneration even when it was regenerated three times. This result showed that the catalysts according to the present invention were regeneratable.

Example 16

(1) Preparation of Support 5.0 g of Sylosphere 1504 (manufactured by FUJI SILYSIA CHEMICAL LTD.) was suspended in 20 ml of distilled water, and 5 ml of an aqueous solution containing 0.125 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 20 ml of an aqueous solution containing 0.0044 g of nickel nitrate hexahydrate was added to the suspension, followed by stirring at room temperature for 10 minutes and heating at 80° C. for 20 hours. The temperature was lowered to room temperature, and the solid formed was filtered, washed with water, dried at 80° C. in air for 3 hours, and calcined at 300° C. for 6 hours to afford a catalyst.

The catalyst was found to contain 0.043 wt % of nickel relative to the support weight and have $SiO_2/Al_2O_3$ of 521 and Ni/Al of 0.14.

(3) Oligomerization Reaction

Reaction was performed as described in Example 1 (3), except that the catalyst obtained in (2) above was used. After the reaction for 24 hours, the ethylene conversion was 24.1%, the selectivity for butenes was 85.8%, and the selectivity for hexenes was 9.4%. The catalyst life was 71 hours. The results are set forth in Table 6.

Example 17

Reaction was performed as described in Example 1 (3), except that the catalyst obtained in Example 16 (2) was used and that the reaction pressure was changed from 0.1 MPa to 0.2 MPa. After the reaction for 24 hours, the ethylene conversion was 36.3%, the selectivity for butenes was 83.5%, and the selectivity for hexenes was 10.8%. The catalyst life was 60 hours. The results are set forth in Table 6.

Example 18

Reaction was performed as described in Example 1 (3), except that the catalyst obtained in Example 16 (2) was used and that the reaction pressure was changed from 0.1 MPa to 0.35 MPa. After the reaction for 24 hours, the ethylene conversion was 49.5%, the selectivity for butenes was 79.4%, and the selectivity for hexenes was 13.5%. The catalyst life was 24 hours. The results are set forth in Table 6.

Example 19

Reaction was performed as described in Example 1 (3), except that the catalyst obtained in Example 16 (2) was used and that the reaction temperature was changed from 300° C. to 250° C. After the reaction for 24 hours, the ethylene conversion was 29.2%, the selectivity for butenes was 87.8%, and the selectivity for hexenes was 9.2%. The catalyst life was 88 hours. The results are set forth in Table 6.

Example 20

Reaction was performed as described in Example 1 (3), except that the catalyst obtained in Example 16 (2) was used and that the reaction temperature was changed from 300° C. to 200° C. After the reaction for 24 hours, the ethylene conversion was 13.2%, the selectivity for butenes was 92.3%, and the selectivity for hexenes was 6.6%. The catalyst life was 163 hours. The results are set forth in Table 6.

Example 21

Reaction was performed as described in Example 1 (3), except that the catalyst obtained in Example 16 (2) was used and that the WHSV was changed from 6.13 h$^{-1}$ to 10.7 h$^{-1}$. After the reaction for 24 hours, the ethylene conversion was 24.5%, the selectivity for butenes was 85.1%, and the selectivity for hexenes was 9.6%. The catalyst life was 69 hours. The results are set forth in Table 6.

Example 22

Reaction was performed as described in Example 1 (3), except that the catalyst obtained in Example 16 (2) was used and that the WHSV was changed from 6.13 h$^{-1}$ to 21.4 h$^{-1}$. After the reaction for 24 hours, the ethylene conversion was 26.7%, the selectivity for butenes was 85.3%, and the selectivity for hexenes was 10.3%. The catalyst life was 72 hours. The results are set forth in Table 6.

Example 23

Reaction was performed as described in Example 1 (3), except that the catalyst obtained in Example 16 (2) was used, that the reaction pressure was changed from 0.1 MPa to 0.35 MPa, and that the WHSV was changed from 6.13 h$^{-1}$ to 2.05 h$^{-1}$. After the reaction for 24 hours, the ethylene conversion was 21.7%, the selectivity for butenes was 91.1%, and the selectivity for hexenes was 7.3%. The catalyst life was 124 hours. The results are set forth in Table 6.

Changes with time of ethylene conversion and selectivity for butenes are shown in FIG. 1.

TABLE 6

|  | Reaction temperature (° C.) | Reaction pressure (MPa) | WHSV (h$^{-1}$) | Ethylene conversion (%) | Selectivity for butenes (%) | Selectivity for hexenes (%) | Life (h) |
| --- | --- | --- | --- | --- | --- | --- | --- |
| Ex. 16 | 300 | 0.1 | 6.13 | 24.1 | 85.8 | 9.4 | 71 |
| Ex. 17 | 300 | 0.2 | 6.13 | 36.3 | 83.5 | 10.8 | 60 |
| Ex. 18 | 300 | 0.35 | 6.13 | 49.5 | 79.4 | 13.5 | 24 |
| Ex. 19 | 250 | 0.35 | 6.13 | 29.2 | 87.8 | 9.2 | 88 |
| Ex. 20 | 200 | 0.35 | 6.13 | 13.2 | 92.3 | 6.6 | 163 |
| Ex. 21 | 300 | 0.35 | 10.7 | 24.5 | 85.1 | 9.6 | 69 |
| Ex. 22 | 300 | 0.35 | 21.4 | 26.7 | 85.3 | 10.3 | 72 |
| Ex. 23 | 200 | 0.35 | 2.05 | 21.7 | 91.1 | 7.3 | 124 |

Example 24

(1) Preparation of Support 5.0 g of Sylosphere 1504 (manufactured by FUJI SILYSIA CHEMICAL LTD.) was suspended in 20 ml of distilled water, and 5 ml of an aqueous solution containing 0.063 g of aluminum nitrate nonahydrate was added to the suspension. The mixture was stirred at room temperature for 10 minutes, and water was distilled away at 70° C. under reduced pressure. The solid thus formed was dried at 80° C. in air for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 20 ml of an aqueous solution containing 0.044 g of nickel nitrate hexahydrate was added to the suspension, followed by stirring at room temperature for 10 minutes and heating at 80° C. for 20 hours. The temperature was lowered to room temperature, and the solid formed was filtered, washed with water, dried at 80° C. in air for 3 hours, and calcined at 300° C. for 6 hours to afford a catalyst.

The catalyst was found to contain 0.09 wt % of nickel relative to the support weight and have $SiO_2/Al_2O_3$ of 1041 and Ni/Al of 0.58.

(3) Oligomerization Reaction

Reaction was performed as described in Example 1 (3), except that the catalyst obtained in (2) above was used. After the reaction for 24 hours, the ethylene conversion was 20.5%, the selectivity for butenes was 86.4%, and the selectivity for hexenes was 8.9%. The catalyst life was 33 hours.

Example 25

(1) Preparation of Support

An autoclave was charged with a solution of 112.5 g of n-dodecyltrimethylammonium bromide in 321 ml of distilled water, a solution of 5.30 g of sodium hydroxide in 63 ml of distilled water, and 153.15 g of SNOWTEX 20 (manufactured by NISSAN CHEMICAL INDUSTRIES, LTD.). These materials were heated to 140° C. and stirred for 48 hours, and the temperature was lowered to room temperature. The solid thus formed was filtered, washed with water, and dried at 80° C. in air for 24 hours to afford 45.51 g of a support containing silica and alumina.

(2) Preparation of Catalyst 8.0 g of the support obtained in (1) above was suspended in 80 ml of distilled water. Subsequently, 80 ml of an aqueous solution containing 0.025 g of nickel nitrate hexahydrate was added to the suspension, followed by stirring at room temperature for 1 hour and heating at 80° C. for 20 hours. The temperature was lowered to room temperature, and the solid formed was filtered, washed with water, dried at 80° C. in air for 3 hours, and calcined at 500° C. for 6 hours to afford a catalyst.

The catalyst was found to contain 0.09 wt % of nickel relative to the support weight and have $SiO_2/Al_2O_3$ of 400 and Ni/Al of 0.24. Properties of the catalyst obtained are set forth in Table 7.

(3) Oligomerization Reaction

Reaction was performed as described in Example 1 (3), except that the catalyst obtained in (2) above was used and that the reaction temperature was changed to 350° C. After the reaction for 24 hours, the ethylene conversion was 45.3%, the selectivity for butenes was 74.5%, and the selectivity for hexenes was 11.0%. The catalyst life was 341 hours. The results are set forth in Table 8.

TABLE 7

|  | Amount of nickel supported (wt %) | $SiO_2/Al_2O_3$ (mol/mol) | Ni/Al (mol/mol) |
| --- | --- | --- | --- |
| Ex. 25 | 0.09 | 400 | 0.24 |

TABLE 8

|  | Reaction temperature (° C.) | Reaction pressure (MPa) | WHSV (h$^{-1}$) | Ethylene conversion (%) | Selectivity for butenes (%) | Selectivity for hexenes (%) | Life (h) |
| --- | --- | --- | --- | --- | --- | --- | --- |
| Ex. 25 | 350 | 0.1 | 6.13 | 45.3 | 74.5 | 11.0 | 341 |

Example 26

(1) Preparation of Support 20.12 g of CARIACT Q-10 (manufactured by FUJI SILYSIA CHEMICAL LTD.) was suspended in 80 ml of distilled water, and 20 ml of an aqueous solution containing 0.502 g of aluminum nitrate nonahydrate was added to the suspension. Water was removed, and the resultant solid was dried at 80° C. for 3 hours and was calcined at 500° C. for 6 hours to afford a support containing silica and alumina.

(2) Preparation of Catalyst 2.0 g of the support obtained in (1) above was suspended in 20 ml of distilled water. Subsequently, 0.5 ml of an aqueous solution prepared by dissolving 0.0042 g of nickel nitrate hexahydrate in 20 ml of distilled water was added to the suspension. Further, 20 ml of distilled water was added, followed by stirring. The mixture was heated at 80° C. for 20 hours. The solid formed was filtered, washed with water, dried at 80° C. for 3 hours, and calcined at 500° C. for 6 hours to afford a catalyst.

The catalyst was found to contain 0.001 wt % of nickel relative to the support weight and have $SiO_2/Al_2O_3$ of 439 and Ni/Al of 0.0023. Properties of the catalyst obtained are set forth in Table 9.

(3) Oligomerization Reaction 0.279 g of the catalyst obtained in (2) above was packed in a fixed bed flow reactor. Nitrogen was passed through the reactor at a rate of 50 ml/min at atmospheric pressure, and the catalyst layer was held at 300° C. for 2 hours. The gas flow was changed from nitrogen to ethylene, which was fed at 250° C., 3.6 MPa and WHSV of 2.15 $h^{-1}$, and thereby ethylene was oligomerized. After the reaction for 29 hours, the ethylene conversion was 39.7%, the selectivity for butenes was 86.6%, and the selectivity for hexenes was 11.2%. The catalyst life was 83 hours. The results are set forth in Table 10.

Example 27

Reaction was performed as described in Example 26 (3), except that the catalyst obtained in Example 26 (2) was used and that the reaction temperature was changed from 250° C. to 300° C. and the WHSV was changed from 2.15 $h^{-1}$ to 6.67 $h^{-1}$. After the reaction for 26 hours, the ethylene conversion was 45.0%, the selectivity for butenes was 84.7%, and the selectivity for hexenes was 12.1%. The catalyst life was 68 hours. The results are set forth in Table 10.

Example 28

(1) Preparation of Catalyst 1.0 g of the support obtained in Example 10 (1) was suspended in 10 ml of distilled water. Subsequently, 0.5 ml of an aqueous solution prepared by dissolving 0.0018 g of nickel sulfate hexahydrate in 40 ml of distilled water was added to the suspension. Further, 10 ml of distilled water was added, followed by stirring. Water was distilled away, and the residue was dried at 80° C. for 3 hours and was calcined at 500° C. for 6 hours to afford a catalyst.

The catalyst was found to contain 0.001 wt % of nickel relative to the support weight and have $SiO_2/Al_2O_3$ of 470 and Ni/Al of 0.0024. Properties of the catalyst obtained are set forth in Table 9.

(2) Oligomerization Reaction

Reaction was performed as described in Example 27 using 0.279 g of the catalyst obtained in (1) above. After the reaction for 26 hours, the ethylene conversion was 36.5%, the selectivity for butenes was 88.8%, and the selectivity for hexenes was 9.5%. The catalyst life was 45 hours. The results are set forth in Table 10.

Example 29

(1) Preparation of Catalyst 2.1 g of the support obtained in Example 11 (1) was suspended in 20 ml of distilled water. Subsequently, 0.5 ml of an aqueous solution prepared by dissolving 0.0041 g of nickel nitrate hexahydrate in 40 ml of distilled water was added to the suspension. Further, 20 ml of distilled water was added, followed by stirring. The mixture was heated at 80° C. for 20 hours. The solid formed was filtered, washed with water, dried at 80° C. for 3 hours, and calcined at 500° C. for 6 hours to afford a catalyst.

The catalyst was found to contain 0.0005 wt % of nickel relative to the support weight and have $SiO_2/Al_2O_3$ of 275 and Ni/Al of 0.0007. Properties of the catalyst obtained are set forth in Table 9.

(2) Oligomerization Reaction

Reaction was performed as described in Example 27, except that 0.574 g of the catalyst obtained in (1) above was used and that the WHSV was changed from 6.67 $h^{-1}$ to 1.0 $h^{-1}$. After the reaction for 26 hours, the ethylene conversion was 35.8%, the selectivity for butenes was 73.9%, and the selectivity for hexenes was 15.4%. The catalyst life was 39 hours. The results are set forth in Table 10.

Comparative Example 5

Reaction was performed as described in Example 27, except that the catalyst from Example 26 (1) was used without supporting nickel. At an initial stage of the reaction, the ethylene conversion was 0%, the selectivity for butenes was 0%, and the selectivity for hexenes was 0%. The reaction was continued for 20 hours thereafter, but the ethylene conversion, the selectivity for butenes and the selectivity for hexenes were all 0%. The results are set forth in Table 10.

Comparative Example 6

(1) Preparation of Support 5.00 g of CARIACT Q-10 (manufactured by FUJI SILYSIA CHEMICAL LTD.) was suspended in 20 ml of distilled water, and 20 ml of an aqueous solution containing 0.125 g of aluminum nitrate nonahydrate was added to the suspension. Water was removed, and the resultant solid was dried at 80° C. for 3 hours and was calcined at 500° C. for 6 hours to afford a support containing silica and alumina.

(2) Preparation of Catalyst 1.1 g of the support obtained in (1) above was suspended in 10 ml of distilled water. Subsequently, an aqueous solution of 0.136 g of nickel nitrate hexahydrate in 40 ml of distilled water was added to the suspension, followed by stirring. Water was removed, and the resultant solid was dried at 80° C. for 3 hours and was calcined at 300° C. for 6 hours to afford a catalyst.

The catalyst was found to contain 1.6 wt % of nickel relative to the support weight and have $SiO_2/Al_2O_3$ of 576 and Ni/Al of 5.66. Properties of the catalyst obtained are set forth in Table 9.

(3) Oligomerization Reaction 0.279 g of the catalyst obtained in (2) above was packed in a fixed bed flow reactor, and reaction was performed as described in Example 27. After the reaction for 1.5 hours, the ethylene conversion was 86.7%, the selectivity for butenes was 50.5%, and the selectivity for hexenes was 11.0%. The catalyst showed the high ethylene conversion at the initial stage of reaction, but the catalyst life was only 7 hours. The results are set forth in Table 10.

It was demonstrated that increasing the amount of nickel supported provided high activity at an initial stage of the reaction, but the catalyst was deactivated quickly and could not ensure stable productivity over long periods.

TABLE 9

|  | Amount of nickel supported (wt %) | $SiO_2/Al_2O_3$ (mol/mol) | Ni/Al (mol/mol) |
|---|---|---|---|
| Ex. 26 | 0.001 | 439 | 0.0023 |
| Ex. 27 | 0.001 | 439 | 0.0023 |
| Ex. 28 | 0.001 | 470 | 0.0024 |
| Ex. 29 | 0.0005 | 275 | 0.0007 |
| Comp. Ex. 5 | 0 | 439 | 0 |
| Comp. Ex. 6 | 1.6 | 576 | 5.66 |

TABLE 10

|  | Reaction temperature (°C.) | Reaction pressure (MPa) | WHSV ($h^{-1}$) | Ethylene conversion (%) | Selectivity for butenes (%) | Selectivity for hexenes (%) | Life (h) |
|---|---|---|---|---|---|---|---|
| Ex. 26 | 250 | 3.6 | 2.15 | 39.7[1] | 86.6[1] | 11.2[1] | 83 |
| Ex. 27 | 300 | 3.6 | 6.67 | 45.0[2] | 84.7[2] | 12.1[2] | 68 |
| Ex. 28 | 300 | 3.6 | 6.67 | 36.5[2] | 88.8[2] | 9.5[2] | 45 |
| Ex. 29 | 300 | 3.6 | 1.0 | 35.8[2] | 73.9[2] | 15.4[2] | 39 |
| Comp. Ex. 5 | 300 | 3.6 | 6.67 | 0[3] | 0[3] | 0[3] | 0 |
| Comp. Ex. 6 | 300 | 3.6 | 6.67 | 86.7[4] | 50.5[4] | 11.0[4] | 7 |

[1] Date after the reaction for 29 hours
[2] Data after the reaction for 26 hours
[3] Data after the reaction for 20 hours
[4] Data after the reaction for 1.5 hours Example 30

In this example, an oligomerization reaction and a disproportionation reaction were carried out in a single reactor.

The catalyst from Example 26 (2) was used as an oligomerization catalyst. Tungsten oxide supported on silica was used as a disproportionation catalyst. The disproportionation catalyst was prepared according to the preparation of Catalyst component A in Example 1 of U.S. Pat. No. 4,575,575. A fixed bed flow reactor was packed with 0.28 g of the oligomerization catalyst and a catalyst mixture consisting of 0.33 g of the disproportionation catalyst and 0.99 g of magnesium oxide (hereinafter, also the disproportionation catalyst/cocatalyst), together with quartz wool and quartz sand as holding materials, so that the total length of the packings became 400 mm.

The oligomerization catalyst and the disproportionation catalyst/cocatalyst were activated by the method described in Example 3 of U.S. Pat. No. 4,575,575 except that hydrogen was used in place of carbon monoxide. The gas flow to the reactor was changed to ethylene at WHSV of 8.9 $h^{-1}$ relative to the oligomerization catalyst, and thereby ethylene was brought into contact with the oligomerization catalyst and oligomerized at 350° C. and 2.86 MPa. Successively, the oligomer from the oligomerization was brought into contact with ethylene in the presence of the disproportionation catalyst/cocatalyst and was thereby disproportionated.

After the reaction for 29 hours, the ethylene conversion was 56.4% and the propylene selectivity was 62.4%. After the reaction for 59 hours, the ethylene conversion was 50.1% and the propylene selectivity was 50.2%. The results of Example 30 show that propylene can be produced stably over a long period with little deterioration of the catalyst according to the present invention.

In the case where by-produced olefins such as butene other than the raw material ethylene and the product propylene are all recycled, the propylene selectivity reaches 97% or more. It is possible to produce propylene with higher selectivity.

The invention claimed is:

1. An ethylene oligomerization catalyst comprising a support and a nickel compound supported on the support, the support containing silica and alumina, wherein:
   the amount of nickel supported is in the range of 0.0001 to 1 wt % based on the weight of the support, and the molar ratio of silica to alumina in the support ($SiO_2/Al_2O_3$) is in the range of 100 to 2000.

2. The ethylene oligomerization catalyst according to claim 1, wherein the molar ratio of nickel to aluminum in the catalyst (Ni/Al) is in the range of 0.00005 to 1.5.

3. The ethylene oligomerization catalyst according to claim 1, wherein the amount of nickel supported is in the range of 0.0001 to 0.5 wt % based on the weight of the support, and the molar ratio of silica to alumina in the support ($SiO_2/Al_2O_3$) is in the range of 100 to 1000.

4. The ethylene oligomerization catalyst according to claim 1, wherein the molar ratio of silica to alumina in the support ($SiO_2/Al_2O_3$) is in the range of 150 to 1000.

5. The ethylene oligomerization catalyst according to claim 1, wherein the molar ratio of nickel to aluminum in the catalyst (Ni/Al) is in the range of 0.00005 to 1.2.

6. The ethylene oligomerization catalyst according to claim 1, wherein the amount of nickel supported is in the range of 0.0001 to less than 0.1 wt % based on the weight of the support.

7. A process for producing ethylene oligomers, comprising oligomerizing ethylene in the presence of the oligomerization catalyst of claim 1.

8. A process for producing ethylene oligomers, comprising oligomerizing ethylene at a temperature of 100 to 400° C. and a pressure of 0.1 to 50 MPa with the oligomerization catalyst of claim 1.

9. The process according to claim 8, wherein the temperature is in the range of 150 to 350° C. and the pressure is in the range of 0.1 to 10 MPa.

10. A process for producing olefins, comprising performing an oligomerization reaction by contacting ethylene with the oligomerization catalyst of claim 1, and successively performing a disproportionation reaction by contacting the oligomers from the oligomerization reaction with ethylene in the presence of a disproportionation catalyst.

* * * * *